US011628235B2

(12) United States Patent
Sung et al.

(10) Patent No.: US 11,628,235 B2
(45) Date of Patent: Apr. 18, 2023

(54) PHOTO-CROSS-LINKABLE SHAPE-MEMORY POLYMER AND PREPARATION METHOD THEREFOR

(71) Applicant: TMD LAB CO. LTD, Seoul (KR)

(72) Inventors: Hak-Joon Sung, Seoul (KR); Yun Ki Lee, Seoul (KR)

(73) Assignee: TMD LAB CO. LTD, Seoul (KR)

( * ) Notice: Subject to any disclaimer, the term of this patent is extended or adjusted under 35 U.S.C. 154(b) by 247 days.

(21) Appl. No.: 16/499,964

(22) PCT Filed: Jan. 26, 2018

(86) PCT No.: PCT/KR2018/001190
§ 371 (c)(1),
(2) Date: Oct. 1, 2019

(87) PCT Pub. No.: WO2018/186575
PCT Pub. Date: Oct. 11, 2018

(65) Prior Publication Data
US 2021/0102023 A1    Apr. 8, 2021

(30) Foreign Application Priority Data
Apr. 4, 2017 (KR) .................. 10-2017-0043732

(51) Int. Cl.
*C08F 299/04* (2006.01)
*A61L 31/04* (2006.01)
(Continued)

(52) U.S. Cl.
CPC ............ *A61L 17/105* (2013.01); *A61L 27/16* (2013.01); *A61L 31/048* (2013.01);
(Continued)

(58) Field of Classification Search
None
See application file for complete search history.

(56) References Cited

U.S. PATENT DOCUMENTS 8,388,674 B2 *   3/2013   Sandhu ................... A61F 2/945
                                                    623/1.15
10,040,880 B2 *  8/2018   Behl ..................... B29C 61/003

FOREIGN PATENT DOCUMENTS

CN          1279077 C       10/2006
JP       2006-198078 A       8/2006
(Continued)

OTHER PUBLICATIONS

Shen et al (Cross-linking and damping properties of poly(caprolactone-co-glycidyl methacrylate), Polymer Journal (2014) 46, 598-608, The Society of Polymer Science, Japan (SPSJ)).*
(Continued)

*Primary Examiner* — Tae H Yoon
(74) *Attorney, Agent, or Firm* — Hammer & Associates, P.C.

(57) ABSTRACT

The present invention relates to a photo-cross-linkable shape-memory polymer and a preparation method therefor. The shape-memory polymer according to one embodiment of the present invention comprises a photo-cross-linkable functional group, and thus a shape-memory polymer having a melting point suitable for a physiological or medical application device can be provided. Particularly, a method for preparing the shape-memory polymer, according to one embodiment of the present invention, uses a catalyst for inducing the simultaneous ring-opening polymerization of two monomers (CL, GMA) during synthesis of the shape-memory polymer, thereby enabling the synthesis time of the shape-memory polymer to be reduced, and shape-memory polymers having various melting points can be readily prepared by controlling the introduction amounts of CL and GMA.

12 Claims, 9 Drawing Sheets

(51) Int. Cl.
*A61L 27/16* (2006.01)
*A61L 17/10* (2006.01)

(52) U.S. Cl.
CPC ..... *C08F 299/0492* (2013.01); *A61L 2430/12* (2013.01); *A61L 2430/38* (2013.01)

(56) References Cited

FOREIGN PATENT DOCUMENTS

| JP | 2011-512909 A | 4/2011 |
|---|---|---|
| JP | 2016-176024 A | 10/2016 |
| WO | WO 2009/108699 A2 | 9/2009 |

OTHER PUBLICATIONS

San-Ping Zhao et al., "Synthesis and Properties of Photopolymerized pH-Sensitive Hydrogels of Methacrylic Acid and Biodegradable PEG-b-PCL Macromer," Iranian Polymer Journal, (vol. 20), (Issue. 4), (p. 329-340), (2011).

Weiwei Xun et al., "Poly(glycidyl methacrylate)-block-poly(ε-caprolactone)-block-poly(glycidyl methacrylate) Triblock Copolymer: synthesis and Use as Mesoporous Silica Porogen," Journal of Macromolecular Science, Part A: Pure and Applied Chemistry, Taylor & Francis (London), (vol. 50), (Issue. 4), (p. 399-410), 2013.

* cited by examiner

[Figure 1]
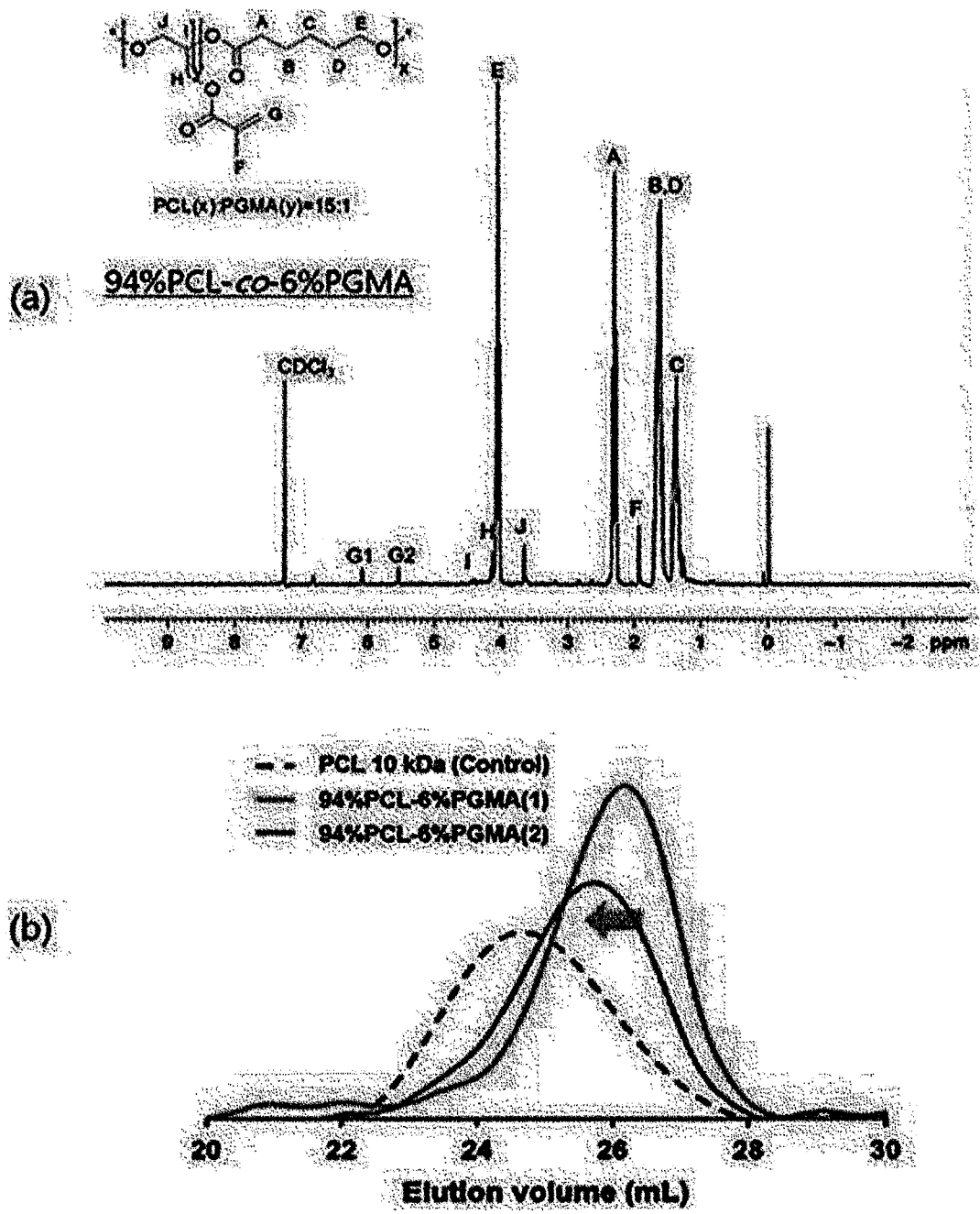

[Figure 2]
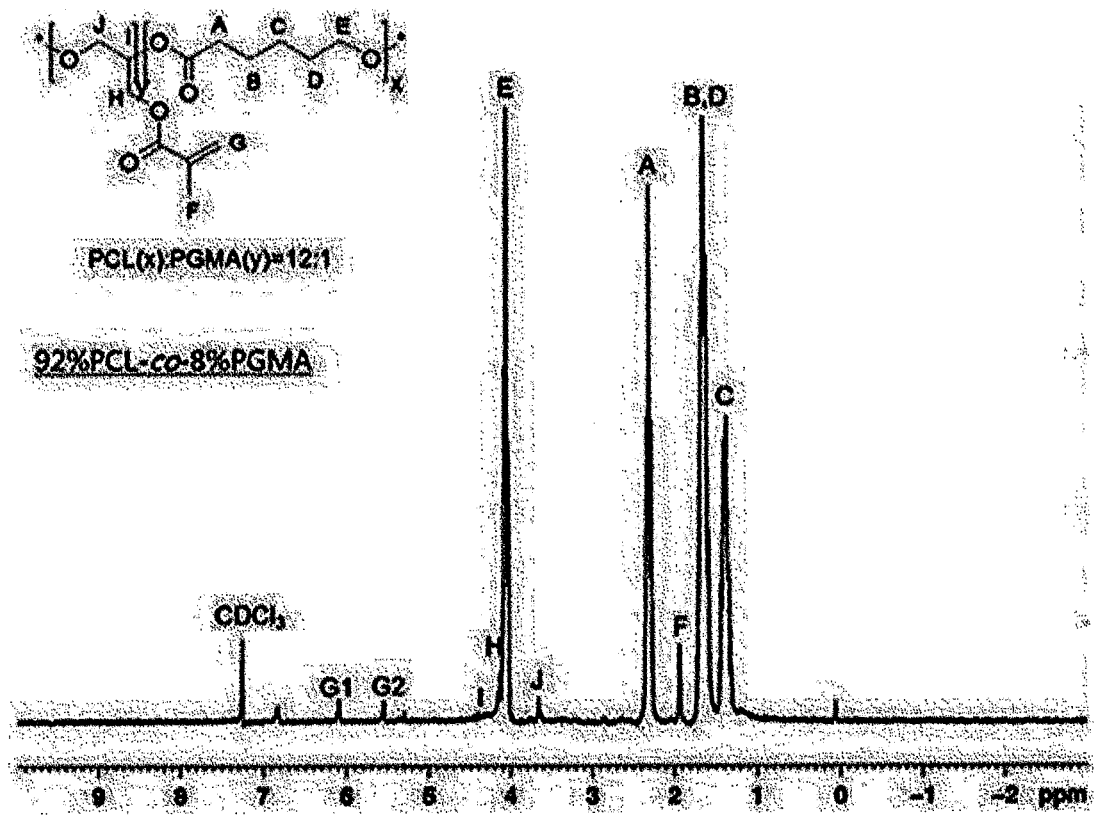

[Figure 3]
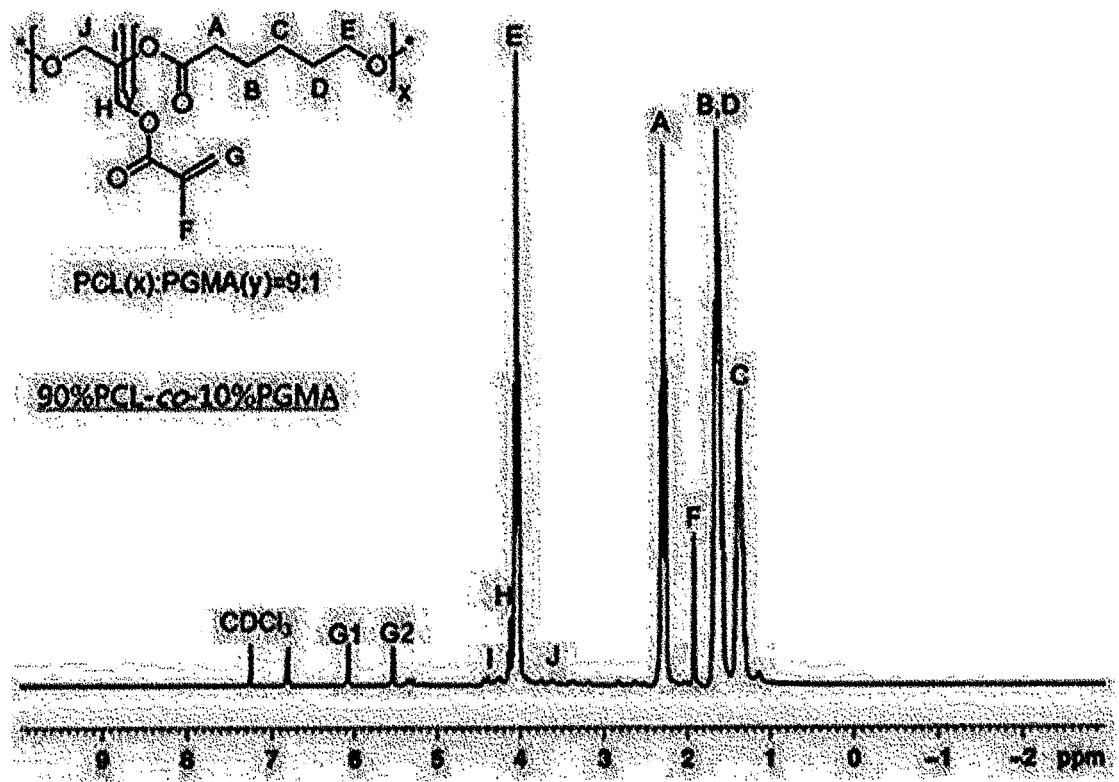

[Figure 4]
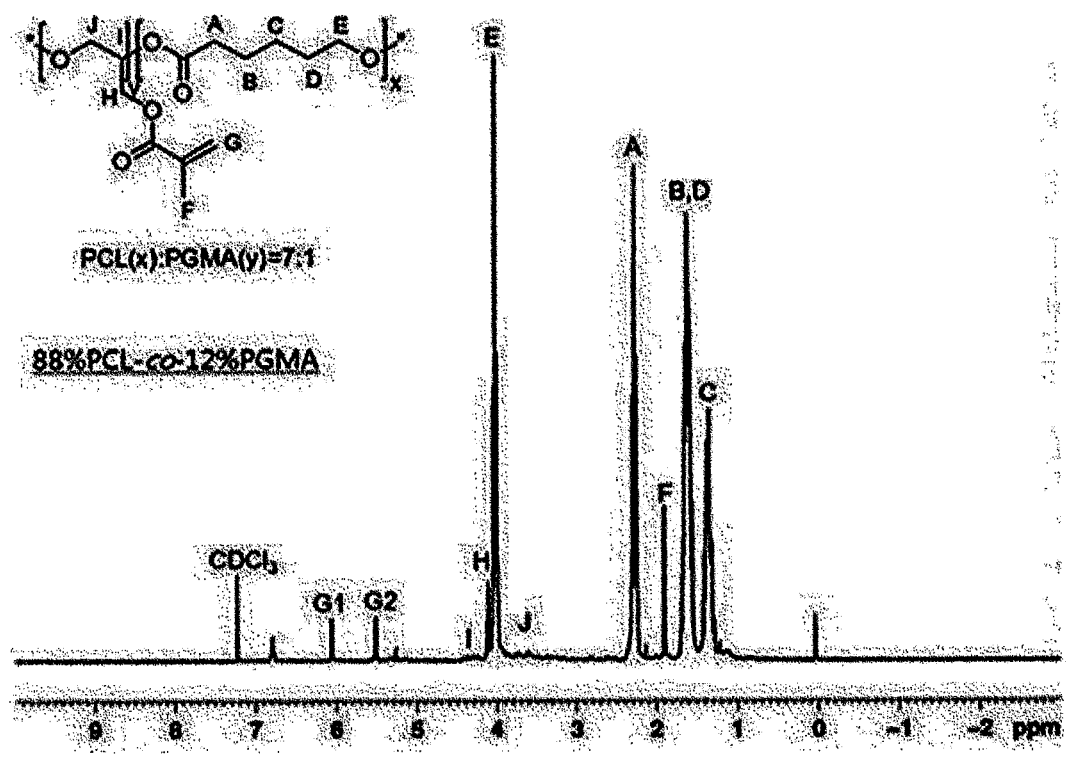

[Figure 5]
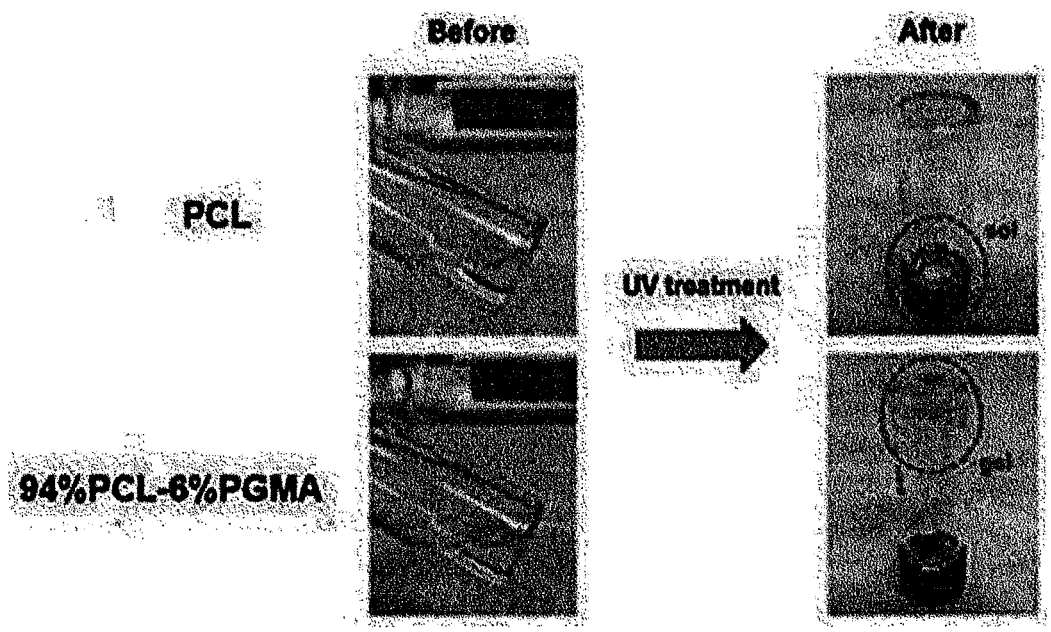

【Figure 6】
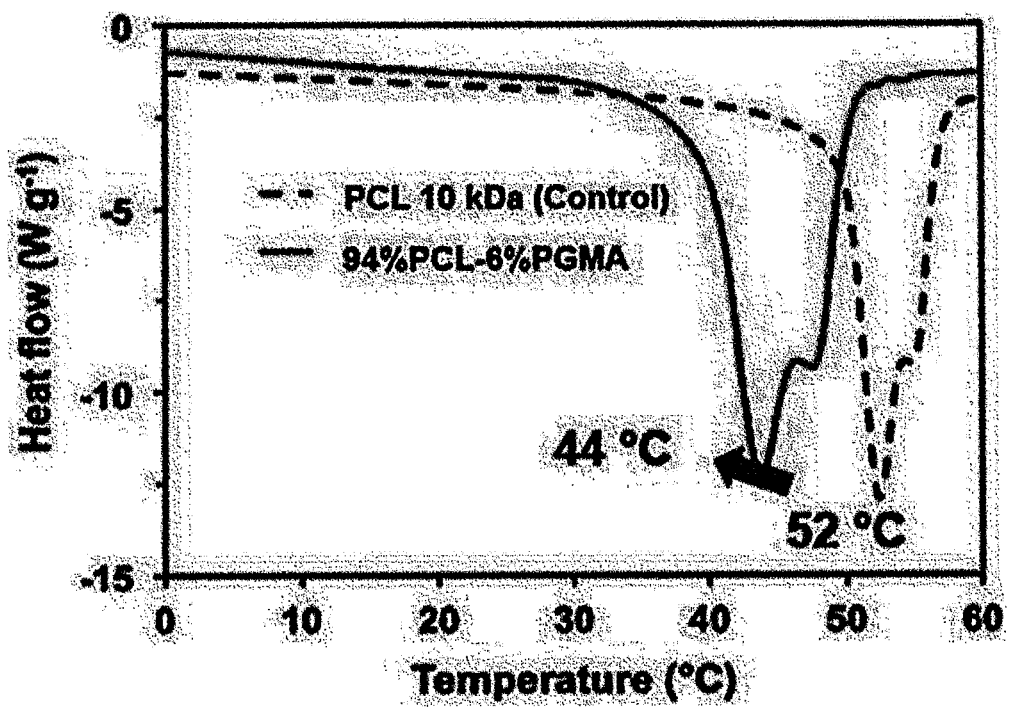

[Figure 7]
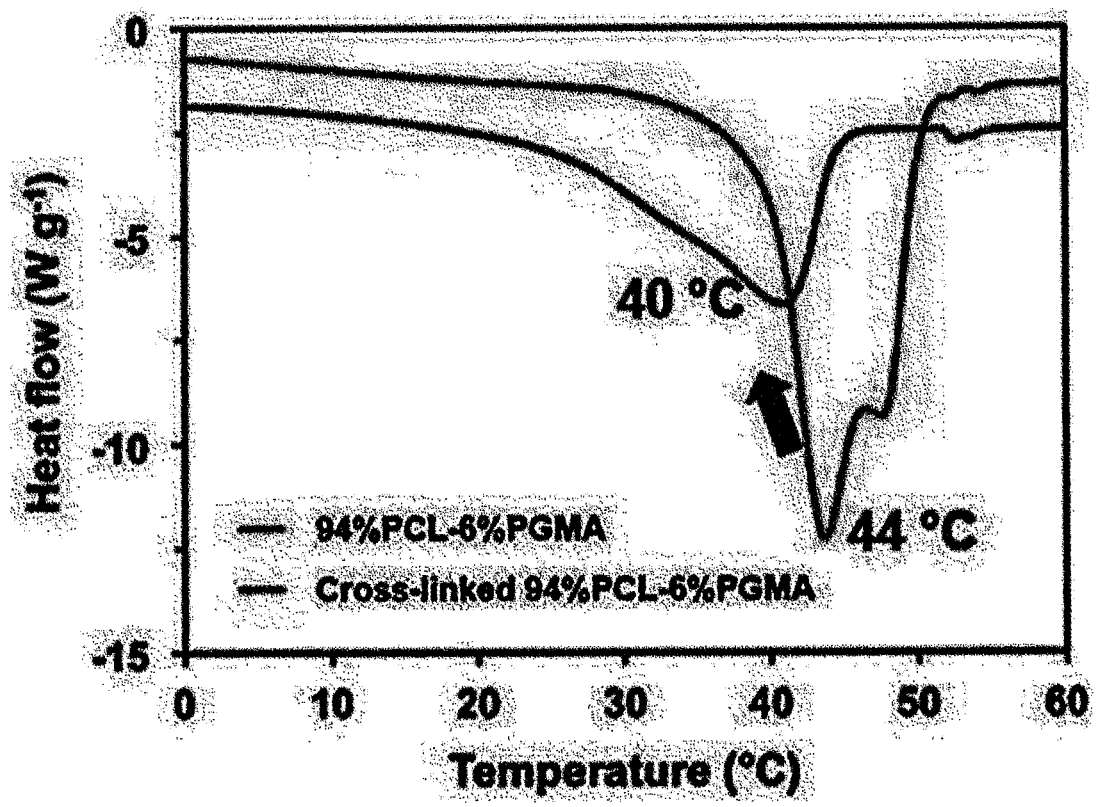

[Figure 8]
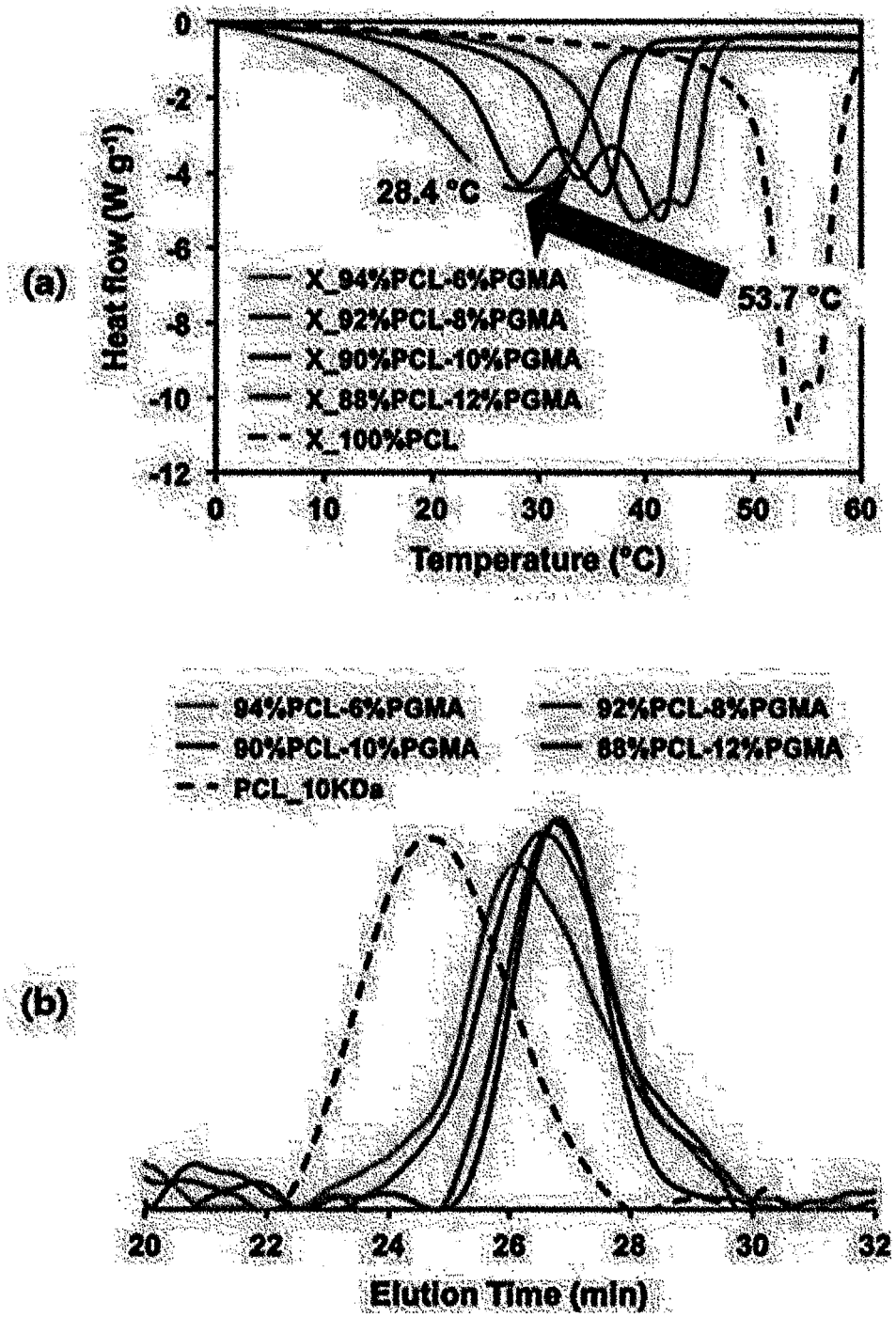

[Figure 9]
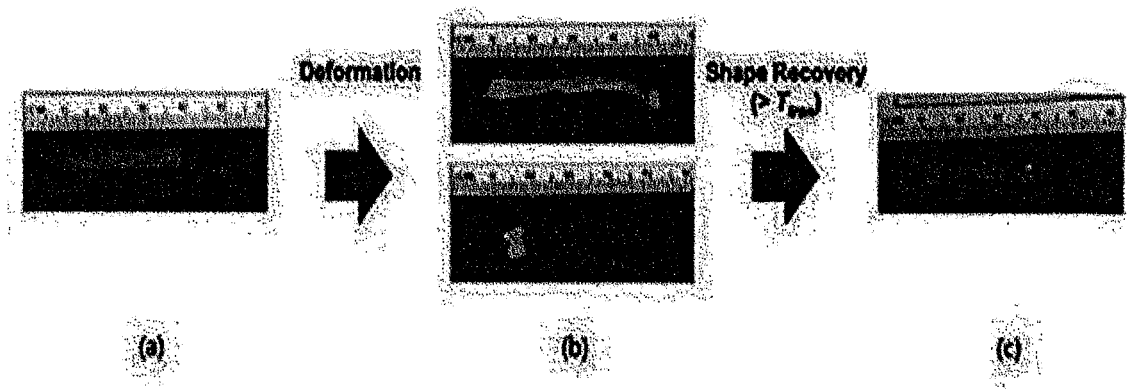

PHOTO-CROSS-LINKABLE SHAPE-MEMORY POLYMER AND PREPARATION METHOD THEREFOR

This application is a 371 application of PCT/KR2018/001190, filed on Jan. 26, 2018, which claimed priority to Korean Application No. 10-2017-0043732, filed on Apr. 4, 2017.

TECHNICAL FIELD

The present invention relates to a photo-cross-linkable shape-memory polymer and a preparation method thereof.

BACKGROUND ART

In recent years, tissue engineering research has come into the spotlight and been ardently conducted to develop an artificial organ capable of replacing the role of a diseased and extracted dysfunctional organ, and the like. Bioimplantation structures prepared using biomaterials are mainly made to replace a lost biological tissue or act as a tissue, and thus much attention has been paid to these structures. In the past, silicone or metals were used, but permanently remained in the human body even after their roles were finished, thereby causing inflammations, or other diseases. Therefore, surgery was needed to remove the silicone or metals.

To solve the above problems, natural or synthetic polymers, which have molding processability as well as biocompatibility, biodegradability, and physical and mechanical properties suitable for processing, have been used.

Among these, the synthetic polymers have mechanical properties superior to the natural polymers and are easily given a functional group, and thus have been more often used compared to the natural polymers. Also, the synthetic polymers have an advantage in that they have a high elastic strain and low prices, and their biodegradation rates may be more readily adjusted.

On the other hand, natural biodegradable polymer materials may include polypeptides such as collagen, gelatin, and the like, polyamino acids such as poly-L-glutamic acid, poly-L-lysine, and the like, and polysaccharides such as alginic acid, chitin, and the like. However, such natural biodegradable polymer materials may not only have limited physical properties but may also have various limitations in terms of processability, mass productivity, and the like.

Therefore, biocompatible synthetic polymers rather than the biodegradable polymers have been more actively researched recently.

More particularly, the synthetic polymers include poly(lactic acid) (PLA), poly(glycolic acid) (PGA), poly(lactic-co-glycolic acid) (PLGA), poly(ε-caprolactone) (PCL), and the like.

Among these, the poly(ε-caprolactone) (PCL) is a biodegradable polymer that is biocompatible, and was approved by the US FDA for biomedical applications in which it may be photo-cross-linked and chemically deformed into shape-memory polymers (SMPs).

However, the PCL has a melting point ($T_m$) of 45 to 65° C., which is too high to be applied to physiological application devices (37° C.), and the like. Therefore, the shape-memory polymers such as poly(ε-caprolactone) (PCL) have limited clinical ability in treating blood vessels and other symptoms. In addition, the use of other shape-memory polymers for therapeutic purposes is limited because it requires functionalization of methacrylates or synthesis of monomers.

Accordingly, there is a need for development of a shape-memory polymer or a method for preparing a shape-memory polymer for treating blood vessels, which is relatively non-invasive, does not causes pain, and can be applied at low cost. Also, there is a need for development of a shape-memory polymer that can be used for medical devices or materials having a melting point suitable for physiological or medical application devices.

DISCLOSURE

Technical Problem

The present invention is designed to solve the problems of the prior art, and therefore it is an object of the present invention to provide a shape-memory polymer capable of being used for medical devices or materials having a melting point suitable for physiological or medical application devices, and a preparation method thereof.

Technical Solution

To achieve the above object, according to one aspect of the present invention, there is provided a shape-memory polymer having a structure represented by the following Formula 1:

[Formula 1]

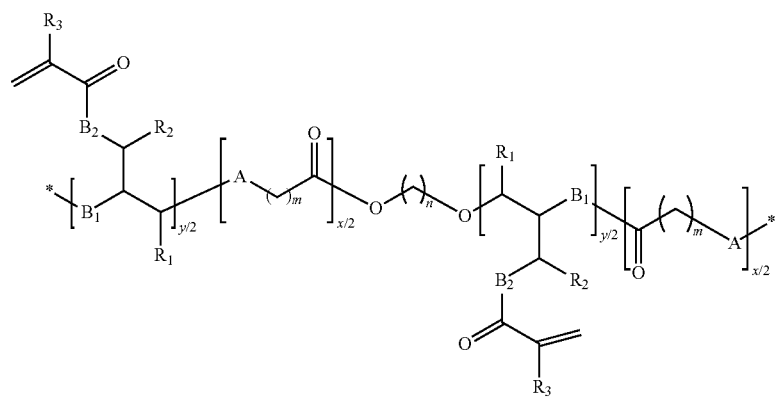

wherein $R_1$, $R_2$, and $R_3$ are each independently hydrogen (H) or an alkyl group having 1 to 6 carbon atoms;

m and n are each independently an integer ranging from 1 to 20;

A, $B_1$, and $B_2$ are each independently oxygen (O) or sulfur (S); and each of x and y represents a molar percentage (mol %) of a repeating unit;

provided that the sum of x and y is 100, and x is in a range of 80 to 98.

According to another aspect of the present invention, there is provided a medical material using the shape-memory polymer represented by Formula 1.

According to still another aspect of the present invention, there is provided a method for preparing a shape-memory polymer, the method including:

performing a polymerization reaction of a mixture including structures represented by Formulas 4 to 6 to prepare a shape-memory polymer:

[Formula 4]

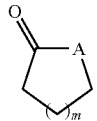

[Formula 5]

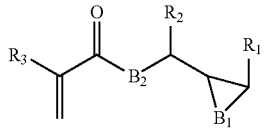

[Formula 6]

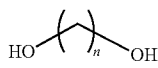

wherein $R_1$, $R_2$, and $R_3$ are each independently hydrogen (H) or an alkyl group having 1 to 6 carbon atoms;

m and n are each independently an integer ranging from 1 to 20; and

A, $B_1$, and $B_2$ are each independently oxygen (O) or sulfur (S).

Advantageous Effects

A shape-memory polymer according to one embodiment of the present invention includes a photo-cross-linkable functional group, and thus a shape-memory polymer having a melting point suitable for physiological or medical application devices can be provided.

Particularly, a method for preparing a shape-memory polymer according to one embodiment of the present invention can use a catalyst for inducing simultaneous ring-opening polymerization of two monomers (CL, GMA) during synthesis of the shape-memory polymer, and thus can be effective in reducing a synthesis time of the shape-memory polymer.

In addition, the method can have an advantage in that shape-memory polymers having various melting points can be readily prepared under the control of amounts of the introduced CL and GMA.

DESCRIPTION OF DRAWINGS

FIG. 1 is a diagram showing the results of $^1$H NMR spectrum and GPC analyses of a shape-memory polymer prepared in Example 1-1 of the present invention (94% PCL-co-6% PGMA).

FIG. 2 is a diagram showing the results of $^1$H NMR spectrum analysis of a shape-memory polymer prepared in Example 1-2 of the present invention (92% PCL-co-8% PGMA).

FIG. 3 is a diagram showing the results of $^1$H NMR spectrum analysis of a shape-memory polymer prepared in Example 1-3 of the present invention (90% PCL-co-10% PGMA).

FIG. 4 is a diagram showing the results of $^1$H NMR spectrum analysis of a shape-memory polymer prepared in Example 1-4 of the present invention (88% PCL-co-12% PGMA).

FIG. 5 is a diagram showing the comparison between phenomena observed after the polymers of Example 1-1 and Comparative Example 1 prepared in the present invention are treated with UV rays.

FIG. 6 is a graph illustrating the DSC analyses of the polymers of Example 1-1 and Comparative Example 1 prepared in the present invention.

FIG. 7 is a graph illustrating the DSC analyses of the polymers of Example 1-1 and Comparative Example 1 prepared in the present invention after the polymers are treated with UV rays.

FIG. 8 is a graph illustrating the characteristics of polymers of Examples 2-1 to 2-4 and Comparative Example 2 prepared in the present invention ((a) DSC analysis, (b) GPC analysis).

FIG. 9 is a diagram showing a material in which a shape-memory polymer deformed at a low temperature is restored to the initial state under deformation temperature conditions ((a) initial state, (b) deformed state at low temperature, and (c) restored state).

BEST MODE

The present invention may be modified in various forms and have various embodiments, and thus particular embodiments thereof will be illustrated in the drawings and described in the detailed description.

However, it should be understood that the description set forth herein is not intended to limit the particular embodiments of the present invention, and encompasses all modifications, equivalents, and substitutions that fall within the spirit and scope of the present invention. In describing the present invention, detailed descriptions with respect to known functions or constructions of the present invention will be omitted when the detailed descriptions are considered to make the gist of the present invention unclear.

The terminology provided herein is merely used for the purpose of describing particular embodiments, and is not intended to limit the present invention. The singular forms "a," "an" and "the" are intended to include the plural forms as well, unless the context clearly indicates otherwise.

It should be understood that the terms "comprises," "comprising," "includes" and/or "including," when used herein, specify the presence of stated features, integers, steps, operations, elements, components and/or combinations thereof, but do not preclude the presence or addition of one or more other features, integers, steps, operations, elements, components and/or combinations thereof.

The present invention relates to a photo-cross-linkable shape-memory polymer, and more particularly, to a shape-memory polymer capable of being used for medical devices or materials having a melting point suitable for physiological or medical application devices.

In the present invention, the term "shape-memory polymer (SMP)" refers to a polymer that has an ability to return to its original state when any object is placed under the same certain conditions (temperature, light, pH, humidity, etc.) as the initial conditions although the object is deformed by external impact after the object is produced under the certain conditions to have a given shape.

Hereinafter, the present invention will be described in detail.

According to one embodiment of the present invention, a shape-memory polymer having a structure represented by the following Formula 1 is provided:

[Formula 1]

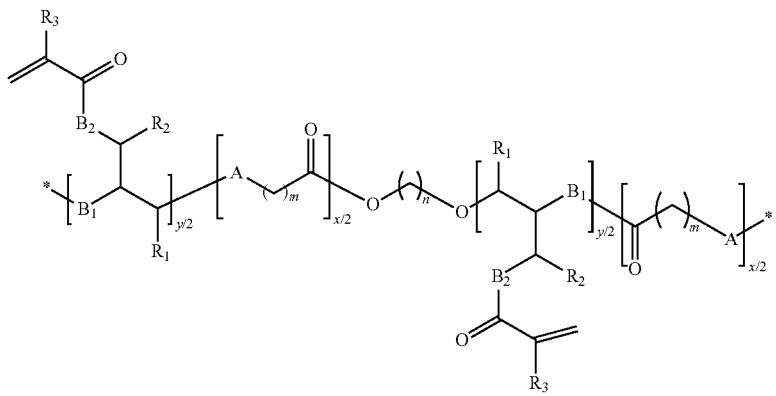

wherein $R_1$, $R_2$, and $R_3$ are each independently hydrogen (H) or an alkyl group ($C_nH_{2n+1}$-) having 1 to 6 carbon (C) atoms;

m and n are each independently an integer ranging from 1 to 20;

A, $B_1$, and $B_2$ are each independently oxygen (O) or sulfur (S); and each of x and y represents a molar percentage (mol %) of a repeating unit;

provided that the sum of x and y is 100, and x is in a range of 80 to 98.

Specifically, in Formula 1, $R_1$, $R_2$, and $R_3$ are each independently hydrogen (H) or a methyl group ($CH_3$—);

m and n are each independently an integer ranging from 3 to 12;

A, $B_1$, and $B_2$ are all oxygen (O); and each of x and y represents a molar percentage (mol %) of a repeating unit;

provided that the sum of x and y is 100, and x is in a range of 80 to 98.

More specifically, in Formula 1, $R_1$, $R_2$, and $R_3$ are each independently hydrogen (H);

m and n are each independently an integer ranging from 5 to 6;

A, $B_1$, and $B_2$ are each independently oxygen (O); and each of x and y represents a molar percentage (mol %) of a repeating unit;

provided that the sum of x and y is 100, and x is in a range of 80 to 98.

As one example, the shape-memory polymer according to the present invention may have a structure represented by the following Formula 2:

[Formula 2]

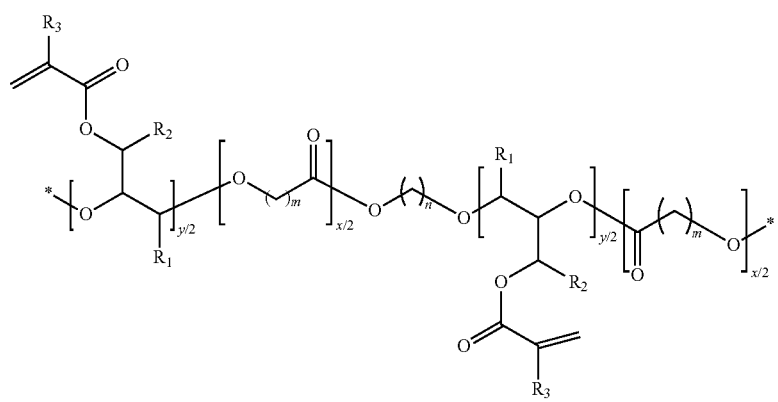

wherein $R_1$, $R_2$, and $R_3$ are each independently hydrogen (H) or an alkyl group having 1 to 6 carbon atoms;

m and n are each independently an integer ranging from 1 to 20; and each of x and y represents a molar percentage (mol %) of a repeating unit;

provided that the sum of x and y is 100, and x is in a range of 80 to 98.

Specifically, the structure of Formula 2 may include a structure represented by the following Formula 3:

[Formula 3]

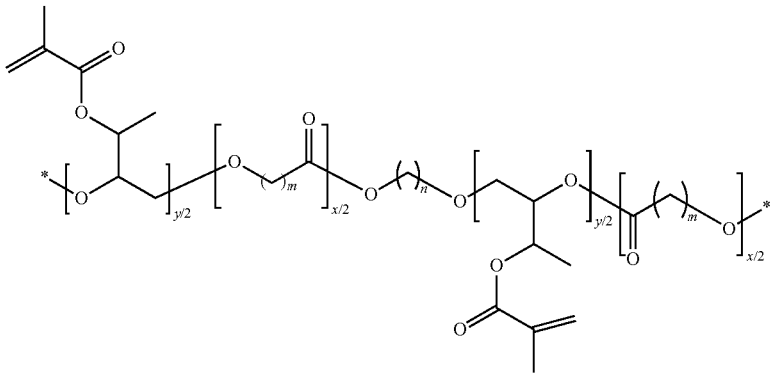

wherein m and n are each independently an integer ranging from 1 to 20; and each of x and y represents a molar percentage (mol %) of a repeating unit; provided that the sum of x and y is 100, and x is in a range of 80 to 98.

The shape-memory polymer according to the present invention may have a structure of a copolymer in which an acrylic monomer containing a glycidyl group is polymerized with an ε-caprolactone monomer. For example, the shape-memory polymer may have a structure of a copolymer [PCL-co-PGMA)] in which glycidyl methacrylate (GMA) is polymerized with an ε-caprolactone monomer (CL).

In the aforementioned shape-memory polymer according to the present invention, the arrangement order of the ε-caprolactone monomer and the acrylic monomer is not particularly limited, and the ε-caprolactone monomer and the acrylic monomer may be arranged in an alternating, random or block fashion.

Also, a hydroxyl group may be bound to an end of the copolymer including the unit represented by Formula 1, 2 or 3. Likewise, the copolymer having a hydroxyl group bound to the end thereof may be prepared by means of polymerization using an initiator having a hydroxyl group bound to the end thereof, and the like.

Meanwhile, the glycidyl group included in the acrylic monomer may be a cross-linkable functional group, and may also be a photo-cross-linkable functional group or thermal cross-linkable functional group.

Meanwhile, the melting point, and the like of the shape-memory polymer according to one embodiment of the present invention may be adjusted depending on the amounts of the ε-caprolactone monomer and the acrylic monomer containing a glycidyl group, both of which constitute the shape-memory polymer according to one embodiment of the present invention.

More specifically, in Formulas 1 to 3, each of x and y represents a molar percentage (mol %) of a repeating unit, provided that the sum of x and y is 100, and x may be in a range of 80 to 98 or 88 to 96.

Here, the term "molar percentage (mol %)" may refer to a ratio of x and y repeating units, and, particularly, may refer to a molar fraction (ratio). As one example, the molar percentage (mol %) may refer to a molar fraction of PCL and PGMA repeating units in the PCL-co-PGMA.

For reference, when x is less than 80 in Formula 1, the melting point of the shape-memory polymer decreases to less than 28° C., which makes it difficult to apply it to the human body due to the shape deformation at room temperature. On the other hand, when x is greater than 98, the melting point of the shape-memory polymer may be greater than 45° C. even after the photo-cross-linking, which makes it difficult to apply it to the human body having a human body temperature (37° C.) due to an increased phase transition temperature of the shape-memory polymer for shape restoration.

Accordingly, the melting point of the shape-memory polymer may be in a range of 30 to 49° C. In this case, the synthesized polymer may be subjected to photo-cross-linking to lower the melting point.

More specifically, the shape-memory polymer after the photo-cross-linking reaction may have an average melting point of 28 to 45° C., 28 to 43° C., or 28 to 42° C.

For reference, as described above, when the melting point of the shape-memory polymer is less than 28° C., the shape deformation in the material may occur at room temperature. Therefore, the shape-memory polymer has limitations in application to physiological application devices. On the other hand, when the melting point of the shape-memory polymer is greater than 45° C., the deformation recovery rate may be less than or equal to 90%. Therefore, problems such as degraded shape memory capacity of the material may occur.

Particularly, because the shape-memory polymer according to one embodiment of the present invention exhibits a deformation recovery rate of 90% or more at a temperature of 28 to 45° C. (including the body temperature), the shape-memory polymer may be widely applied to physiological or medical application devices or medical materials.

The medical materials may be, but are not limited to the following, a material for blood vessel transplantation. In this case, the material for blood vessel transplantation may be a support for blood vessel transplantation or a stent for blood vessel transplantation.

In addition, the medical materials may also be used for a support for blood vessel anastomosis, a conduit for blood vessel transplantation, a material for tooth transplantation, a conduit for organ transplantation, a prosthesis for insertion into the human body, a prosthesis for spinal transplantation, a surgical suture, a platform for drug delivery (a carrier), or a nerve conduit. Meanwhile, the conduit for organ transplantation refers to an implant tube for the urethra, esophagus, and the like.

Also, according to one embodiment of the present invention, a method for preparing a shape-memory polymer is provided, which includes performing a polymerization reaction of a mixture including structures represented by Formulas 4 to 6:

[Formula 4]

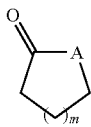

[Formula 5]

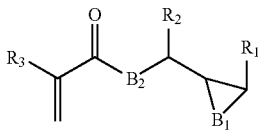

[Reaction Scheme 1]

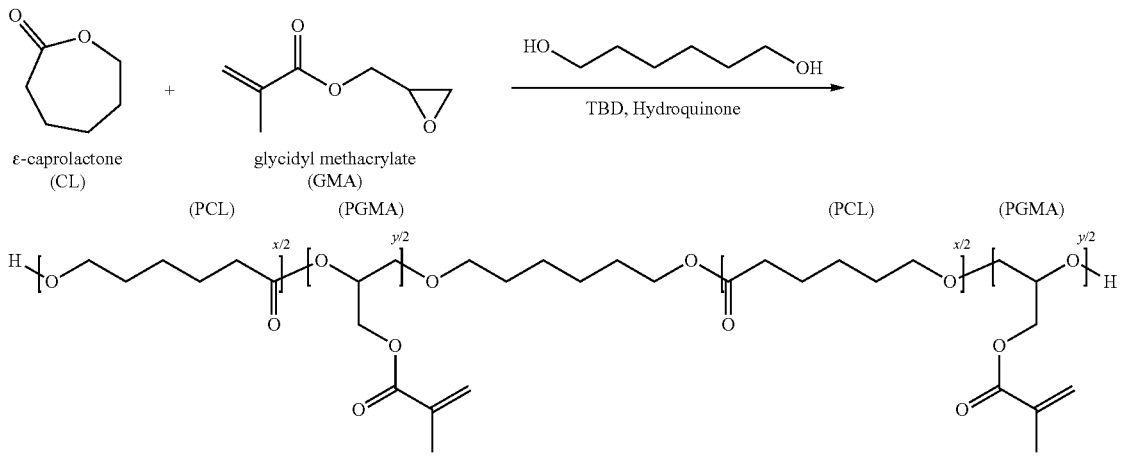

-continued

[Formula 6]

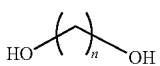

wherein $R_1$, $R_2$, and $R_3$ are each independently hydrogen (H) or an alkyl group ($C_nH_{2n+1}$—) having 1 to 6 carbon (C) atoms;

m and n are each independently an integer ranging from 1 to 20; and

A, $B_1$, and $B_2$ are each independently oxygen (O) or sulfur (S).

As described above, the shape-memory polymer according to the present invention may have a structure of a copolymer in which an acrylic monomer containing a glycidyl group is polymerized with an ε-caprolactone monomer. For example, the shape-memory polymer may have a structure of a copolymer [PCL-co-PGMA] in which glycidyl methacrylate (GMA) is polymerized with an ε-caprolactone monomer (CL).

In this case, the structure of Formula 6 may be an initiator used to perform a chain reaction. As one example, 1,6-hexanediol may be used as the initiator. Particularly, the structures of Formulas 4 and 5 may be condensation-polymerized with respect to the structure of Formula 6 during the polymerization reaction, and may be arranged with respect to the structure of Formula 6 in an alternating, random or block fashion.

As one example, a method for preparing a shape-memory polymer having a structure of a copolymer [PCL-co-PGMA)] includes:

first mixing the monomers, that is, ε-caprolactone (CL) and glycidyl methacrylate (GMA), at a proper molar ratio, adding a catalyst compound to the resulting mixture, and allowing the mixture to react at a reaction temperature of 80 to 140° C.

Then, when the mixture is judged to be thermally stabilized, the shape-memory polymer may be prepared by adding an initiator, performing a copolymerization reaction, washing a polymerized product, purifying the polymerized product by filtration, and drying the polymerized product.

As one example, a polymerization mechanism of the PCL-co-PGMA shape-memory polymer according to one embodiment of the present invention is as follows.

As described above, the method for preparing a shape-memory polymer according to one embodiment of the present invention includes performing a copolymerization reaction of the monomers, that is, ε-caprolactone (CL) and glycidyl methacrylate (GMA).

In addition, the catalyst may be 1,5,7-triazabicyclo[4.4.0]dec-5-ene (TBD), tin(II) (2-ethylhexanoate), trimethylopropane tris(3-mercaptopropionate), or zinc succinate. As one example, the TBD may be used as the catalyst because of its possible high yield and small quantity.

The amount of the catalyst used is not limited, but may be used in an amount of 0.5 to 1 mole in contrast to starting materials.

Particularly, the 1,5,7-triazabicyclo[4.4.0]dec-5-ene (TBD) is a compound for inducing a simultaneous ring-opening polymerization of the two monomers (CL, GMA), and has an effect of shortening a synthesis time of the shape-memory polymer.

At a time point when there is nearly no polymerization conversion rate, that is, during the initial reaction, a polymerization inhibitor may be added along with an HD initiator before addition of the GMA monomer to suppress a reaction between acrylic groups of the GMA sensitive to temperature In addition, the polymerization inhibitor serves to suppress an exothermic reaction locally occurring at the end of polymerization and remove unreacted residual radicals to terminate the reaction. In this case, one or more selected from the group consisting of hydroquinone (HQ), hydroquinone monomethyl ether, p-benzoquinone, and phenothiazine may be used as the polymerization inhibitor, but the present invention is not limited thereto.

In this case, the preparation of the shape-memory polymer may include preparing the shape-memory polymer at an average polymerization temperature of 80 to 140° C., or 100 to 130° C. More specifically, when the polymer synthesis is carried out at a temperature of less than 100° C., a catalyst reaction may not occur. On the other hand, when the polymer synthesis is carried out at a temperature of greater than 130° C., a catalyst reaction rate may be degraded.

In addition, the method may further include inducing a photo-cross-linking reaction in the polymerized shape-memory polymer.

Particularly, the melting point may be further lowered by inducing a photo-cross-linking reaction in the synthesized shape-memory polymer. As one example, the melting point may be lowered to a temperature of 28 to 45° C. by irradiating the polymer with ultraviolet (UV) rays of 320 to 500 nm.

Mode for Invention

Hereinafter, the present invention will be described in further detail with reference to Examples and Experimental Examples thereof.

However, it should be understood that the following Examples and Experimental Examples are merely illustrative of the present invention in detail and are not intended to limit the scope of the present invention.

Experimental Preparation

1: Samples and Devices

ε-caprolactone (CL), hydroquinone (HQ), 1,5,7-triazabi-cyclo[4.4.0]dec-5-ene (TBD), glycidyl methacrylate (GMA), acetonitrile, chloroform, dichloromethane, diethyl ether, 2,2-dimethoxy-2-phenylacetophenone, and 1,6-hexanediol (HD) were purchased from Sigma-Aldrich.

Meanwhile, the melting point and the heat of fusion were measured from a mass of a sample ranging from 5 to 10 mg in an aluminum pan using differential scanning calorimetry (DSC) equipment (commercially available from TA Instrument Inc.). Then, the rate of a lamp was 10° C./min, and measured once at a temperature ranging from −80° C. to 100° C. (including a constant temperature for 3 minutes).

In addition, the number-average of molecular weight ($M_n$) was measured using gel permeation chromatography (GPC) equipment (commercially available from Shimadzu Scientific Instruments Inc.). In this case, the columns used were Shodex 802, 803, and 804, the solvent used was chloroform, and the flow rate was measured to be 1.0 mL/min.

Also, the polymer UV cross-linking was determined using UV/visible ray cross-linking equipment (commercially available from Lumen Dynamics Group Inc.). In this case, the intensity of the lamp used was 14 W/cm$^2$, and the measurement time was 10 minute.

EXAMPLES

Example 1: Synthesis of PCL-co-PGMA Shape-Memory Polymer 1-1: Synthesis of 94% PCL-co-6% PGMA The following reactant input ratio of $[CL]_0/[GMA]_0/[HD]_0/[TBD]_0/[HQ]_0=90/10/1/1/0.5$ was used to synthesize 94% PCL-co-6% PGMA (see Table 1).

TABLE 1

|  | CL (mmol) | GMA (mmol) | HQ (mmol) | TBD (mmol) | HD (mmol) |
| --- | --- | --- | --- | --- | --- |
| Example 1-1 | 90 | 10 | 1 | 1 | 0.5 |

First, CL (90 mmol, 9.97 mL), HD (0.5 mmol, 60 mg), and HQ (1 mmol, 110 mg) were put into a glass reactor (250 mL) and mixed, and then GMA (10 mmol, 1.36 mL) was injected into the glass reactor 10 minutes later.

Then, when an inner temperature of the glass reactor in which the two monomers were mixed was judged to be thermally stabilized, TBD (1 mmol, 140 mg) was dissolved in 1 mL of acetonitrile as the catalyst for inducing the simultaneous ring-opening polymerization of CL and GMA. Thereafter, the resulting mixture was injected into the glass reactor, and stirred at 110° C. for 2 hours. The entire procedure was performed under high-purity nitrogen.

After the reaction, the reaction product was dissolved in 10 mL of chloroform, and precipitated while slowly dropping the reaction product in diethyl ether (400 mL). Then, the precipitate was filtered through a filter paper, and the solvent was removed using a rotary evaporator. Then, the precipitate was dried under reduced pressure to synthesize a PCL-co-PGMA polymer.

Then, the components (the ratio of the PCL and PGMA repeating units through the ratio of the number of hydrogen atoms in the PCL and PGMA) of the synthesized polymer were measured using $^1$H nuclear magnetic resonance ($^1$H NMR). The measurement results are shown in FIG. 1A.

Referring to FIG. 1A, the repeating unit percentage (%) of the ratio of the PCL and PGMA repeating units (PCL:PGMA=15:1) was calculated through the $^1$H NMR analysis based on the chemical structure of the synthetic polymer. The 94% PCL-co-6% PGMA was confirmed in the case of Example 1-1.

In addition, referring to FIG. 1B, the molecular weight of the 94% PCL-co-6% PGMA (1-HD 0.5 mmol, 2-HD 0.25 mmol) polymer was determined through GPC analysis. As a result, it was confirmed that the polymer had a molecular weight ($M_w$) below a desired $M_w$ level of 10 kDa. Thus, the molecular weight ($M_w$) of PCL-co-PGMA may be readily adjusted by adjusting an amount of the initiator added.

1-2: Synthesis of 92% PCL-co-8% PGMA

The following reactant input ratio of $[CL]_0/[GMA]_0/[HD]_0/[TBD]_0/[HQ]_0=86/14/1/1.4/0.5$ was used to synthesize 92% PCL-co-8% PGMA (see Table 2).

TABLE 2

|  | CL (mmol) | GMA (mmol) | HQ (mmol) | TBD (mmol) | HD (mmol) |
| --- | --- | --- | --- | --- | --- |
| Example 1-2 | 86 | 14 | 1.4 | 1 | 0.5 |

Hereinafter, the polymerization reaction was performed in the same manner as in Example 1-1.

Then, the components (the ratio of the PCL and PGMA repeating units through the ratio of the number of hydrogen atoms in the PCL and PGMA) of the synthesized polymer were measured using $^1$H nuclear magnetic resonance ($^1$H NMR). The measurement results are shown in FIG. 2.

Referring to FIG. 2, the repeating unit percentage (%) of the ratio of the PCL and PGMA repeating units (PCL:PGMA=12:1) was calculated through the $^1$H NMR analysis. The repeating unit percentage was confirmed to be 92% PCL-co-8% PGMA in the case of Example 1-2.

1-3: Synthesis of 90% PCL-co-10% PGMA

The following reactant input ratio of $[CL]_0/[GMA]_0/[HD]_0/[TBD]_0/[HQ]_0=82/18/1.8/1/0.5$ was used to synthesize 90% PCL-co-10% PGMA (see Table 3).

TABLE 3

|  | CL (mmol) | GMA (mmol) | HQ (mmol) | TBD (mmol) | HD (mmol) |
| --- | --- | --- | --- | --- | --- |
| Example 1-3 | 82 | 18 | 1.8 | 1 | 0.5 |

Hereinafter, the polymerization reaction was performed in the same manner as in Example 1-1.

Then, the components (the ratio of the PCL and PGMA repeating units through the ratio of the number of hydrogen atoms in the PCL and PGMA) of the synthesized polymer were measured using $^1$H nuclear magnetic resonance ($^1$H NMR). The measurement results are shown in FIG. 3.

Referring to FIG. 3, the repeating unit percentage (%) of the ratio of the PCL and PGMA repeating units (PCL:PGMA=9:1) was calculated through the $^1$H NMR analysis. The repeating unit percentage was confirmed to be 90% PCL-co-10% PGMA in the case of Example 1-3.

1-4: Synthesis of 88% PCL-co-12% PGMA

The following reactant input ratio of $[CL]_0/[GMA]_0/[HD]_0/[TBD]_0/[HQ]_0=78/22/2.2/1/0.5$ was used to synthesize 88% PCL-co-12% PGMA (see Table 4).

TABLE 4

|  | CL (mmol) | GMA (mmol) | HQ (mmol) | TBD (mmol) | HD (mmol) |
| --- | --- | --- | --- | --- | --- |
| Example 1-4 | 78 | 22 | 2.2 | 1 | 0.5 |

Hereinafter, the polymerization reaction was performed in the same manner as in Example 1-1.

Then, the components (the ratio of the PCL and PGMA repeating units through the ratio of the number of hydrogen atoms in the PCL and PGMA) of the synthesized polymer were measured using $^1$H nuclear magnetic resonance ($^1$H NMR). The measurement results are shown in FIG. 4.

Referring to FIG. 4, the repeating unit percentage (%) of the ratio of the PCL and PGMA repeating units (PCL:PGMA=7:1) was calculated through the $^1$H NMR analysis. The repeating unit percentage was confirmed to be 88% PCL-co-12% PGMA in the case of Example 1-4.

Example 2: Synthesis of PCL-co-PGMA Shape-Memory Polymer

Polymers were respectively synthesized at reactant input ratios of $[CL]_0/[GMA]_0/[HD]_0/[TBD]_0/[HQ]_0$ as described below (Examples 2-1 to 2-4).

TABLE 5

|  | CL (mmol) | GMA (mmol) | HQ (mmol) | TBD (mmol) | HD (mmol) |
| --- | --- | --- | --- | --- | --- |
| Example 2-1 | 90 | 10 | 1 | 0.5 | 0.5 |
| Example 2-2 | 86 | 14 | 1.4 | 0.5 | 0.5 |
| Example 2-3 | 82 | 18 | 1.8 | 0.5 | 0.5 |
| Example 2-4 | 78 | 22 | 2.2 | 0.5 | 0.5 |

Specifically, in Examples 2-1 to 2-4, CL, HD, and HQ were put into a glass reactor (250 mL), and then mixed. After 10 minutes, GMA was injected into the glass reactor (see Table 5).

In addition, when an inner temperature of the glass reactor in which the two monomers were mixed was judged to be thermally stabilized, TBD (1 mmol, 140 mg) was dissolved in 1 mL of acetonitrile as the catalyst for inducing the simultaneous ring-opening polymerization of CL and GMA. Thereafter, the resulting mixture was injected into the glass reactor, and stirred at 110° C. for 2 hours. Hereinafter, the polymerization reaction was performed in the same manner as in Example 1-1.

Next, the polymers synthesized in Examples 2-1 to 2-4 were irradiated with UV rays (320 to 500 nm) having an intensity of 14 W/cm$^2$ for 10 minutes to prepare a photocross-linkable shape-memory polymer.

COMPARATIVE EXAMPLES

Comparative Example 1: Polymerization of poly(ε-caprolactone) (PCL)

Polymerization was carried out at the following reactant input ratio of $[CL]_0/[HD]_0/[TBD]_0=100/0.5/1$.

CL (100 mmol, 9.97 mL) and HD (0.5 mmol, 60 mg) were put into a glass reactor (250 mL), and mixed (see Table 6).

TABLE 6

|  | HD (mmol) | TBD (mmol) | HQ (mmol) | CL (mmol) | GMA (mmol) |
| --- | --- | --- | --- | --- | --- |
| Comparative Example 1 | 0.5 | 1 | — | 100 | — |

Next, when an inner temperature of the glass reactor in which the two monomers were mixed was judged to be thermally stabilized, TBD (1 mmol, 140 mg) was dissolved in 1 mL of acetonitrile as the catalyst for inducing ring-opening polymerization of CL. Thereafter, the resulting mixture was injected into the glass reactor, and stirred at 110° C. for 30 minutes. Hereinafter, the polymerization reaction was performed in the same manner as in Example 1-1.

Comparative Example 2: Polymerization of poly(ε-caprolactone) (PCL)—2

Polymerization was carried out at the following reactant input ratio of $[CL]_0/[HD]_0/[TBD]_0=100/0.5/0.5$.

CL (100 mmol, 9.97 mL) and HD (0.5 mmol, 60 mg) were put into a glass reactor (250 mL), and mixed (see Table 7).

TABLE 7

|  | HD (mmol) | TBD (mmol) | HQ (mmol) | CL (mmol) | GMA (mmol) |
|---|---|---|---|---|---|
| Comparative Example 2 | 0.5 | 0.5 | — | 100 | — |

Next, when an inner temperature of the glass reactor in which the two monomers were mixed was judged to be thermally stabilized, TBD (0.5 mmol, 70 mg) was dissolved in 1 mL of acetonitrile as the catalyst for inducing the ring-opening polymerization of CL. Thereafter, the resulting mixture was injected into the glass reactor, and stirred at 110° C. for an hour. Hereinafter, the polymerization reaction was performed in the same manner as in Example 1.

EXPERIMENTAL EXAMPLE

Experimental Example 1: Characterization of Shape-Memory Polymer Prepared in Example 1

1-1: Preparation of Shape-Memory Polymer Material Through UV Cross-Linking

FIG. 5 is a diagram showing the comparison between phenomena observed after the polymers synthesized in Example 1-1 and Comparative Example 1 are treated with UV rays.

Referring to FIG. 5, each of the polymers synthesized in Example 1-1 and Comparative Example 1 was mixed with a photoinitiator at a volume ratio of 10:1, and 400 μL of the resulting mixture was then put into a transparent glass container.

More specifically, 50% by weight of each of the polymers synthesized in Example 1-1 and Comparative Example 1 was dispersed in dichloromethane, and 10% by weight of a photoinitiator was dispersed in dichloromethane. Thereafter, the dispersed solutions were mixed at a volume ratio of 10:1.

Next, the glass container was irradiated with UV rays (320 to 500 nm) having an intensity of 14 W/cm² for 10 minutes.

Then, each of the UV-treated containers was turned upside down.

As a result, it can be seen that the polymer prepared in Example 1-1 was attached to a bottom surface of the glass container, and thus a gel was cross-linked due to the cross-linking between modified acrylic groups during the UV treatment. On the other hand, it can be seen that the polymer of Comparative Example 1 was in a liquid state, and thus the state of the material was not changed.

That is, it can be seen that the polymer synthesized in Example 1-1 was cross-linkable by irradiation with UV rays.

1-2: DSC Analysis-1

FIG. 6 and Table 8 show the DSC analyses of the polymers of Example 1 and Comparative Example 1, respectively.

More specifically, to analyze the physical properties of the polymer affected by the components and design variables, the physical properties were measured using differential scanning calorimetry (DSC) ($T_m$; melting temperature, $H_m$; melting enthalpy, $T_c$; crystallization temperature, and $H_c$; crystallization enthalpy).

TABLE 8

| Polymer | $T_m$ (° C.) | $H_m$ (J/g) | $T_c$ (° C.) | $H_c$ (J/g) |
|---|---|---|---|---|
| Comparative Example 1 | 52.41 | 78.85 | 24.13 | 79.49 |
| Example 1 | 43.76 | 55.97 | 20.95 | 57.00 |

Referring to FIG. 6 and Table 8, it can be seen that, in comparison of the melting points, the melting point of the PCL-co-PGMA synthesized in Example 1 was further lowered, compared to when the PCL of Comparative Example 1 was synthesized alone.

1-3: DSC Analysis-2

FIG. 7 and Table 9 show the DSC analyses of the polymers of Example 1-1 and Comparative Example 1, respectively, after the polymers are treated with UV rays.

TABLE 9

| Polymers | $XT_m$ (° C.) | $H_m$ (J/g) | $XT_c$ (° C.) | $H_c$ (J/g) |
|---|---|---|---|---|
| Comparative Example 1 | 52.05 | 67.17 | 23.17 | 65.17 |
| Example 1 | 40.44 | 43.01 | −1.73 | 26.32 |

Referring to FIG. 7 and Table 9, it can be seen that the melting point of the PCL-co-PGMA synthesized in Example 1-1 was further lowered, compared to when the PCL of Comparative Example 1 was synthesized alone. In particular, it can be seen that, after the polymer synthesized in Example 1 was treated with UV rays, the melting point of the polymer was 40.44° C., which was lower than when the polymer was not treated with UV rays.

Experimental Example 2: Characterization of Examples 2-1 to 2-5 and Comparative Example 2

In Experimental Example 2, the melting points of the polymers synthesized in Examples 2-1 to 2-4 and Comparative Example 2 were measured, and the UV-treated shape-memory polymers were subjected to DSC and GPC analyses.

The results are shown in FIG. 8 and listed in Table 10 below (FIG. 8A: DSC analyses, and FIG. 8B: GPC analyses).

TABLE 10

|  | x % PCL-y % PGMA | CL (mmol) | GMA (mmol) | HQ (mmol) | GMA (%) | $T_m$ (° C.) | $XT_m$ (° C.) |
|---|---|---|---|---|---|---|---|
| Comparative Example 2 | 100% PCL | 100 | — | — | — | 52.4 | 53.7 |
| Example 2-1 | 94% PCL-6% PGMA | 90 | 10 | 1 | 6.1 | 45.2 | 41.4 |
| Example 2-2 | 92% PCL-8% PGMA | 86 | 14 | 1.4 | 8.1 | 40.4 | 39.3 |
| Example 2-3 | 90% PCL-10% PGMA | 82 | 18 | 1.8 | 10.6 | 39.6 | 36.0 |
| Example 2-4 | 88% PCL-12% PGMA | 78 | 22 | 2.2 | 12.0 | 35.6 | 28.4 |

Referring to FIG. 8 and Table 10, it can be seen that, when the characteristics of the polymers of Examples 2-1 to 2-4 and Comparative Example 2 were compared, the melting points of the PCL-co-PGMA shape-memory polymers synthesized in Examples 2-1 to 2-4 were further lowered, compared to when the PCL was synthesized alone in the case of Comparative Example 2.

In particular, it can be seen that the melting point was lowered with an increasing content of GMA. Also, it can be seen that the melting point ($XT_m$) of the polymer after the UV treatment was further lowered, compared to when the polymer was not treated with UV rays.

In addition, referring to FIG. 8, the molecular weights of the polymers were determined through the GPC analysis. As a result, it can be seen that the polymers had a molecular weight ($M_w$) below a desired $M_w$ level of 10 kDa. In particular, it can be seen that the molecular weight of the polymers was lowered with an increasing content of GMA, indicating that the amorphous PGMA destroyed PCL crystallinity to lower the $T_m$ and % crystallinity.

Experimental Example 3: Restoration of Shape-Memory Polymer

The shape memory characteristics of the shape-memory polymer synthesized in Example 1 are shown in FIG. 9 ((A) initial state, (B) deformed state, and (C) restored state).

More specifically, it can be seen that the shape-memory polymer material synthesized in Example 1 was deformed from the initial state when the shape-memory polymer material was thermally treated at 60° C. (FIG. 9B). Also, it can be seen that the shape-memory polymer material was restored to the initial state when the temperature was adjusted to an initial temperature of 35 to 40° C.

Next, the deformation recovery rate was measured.

The deformation recovery rate was determined, as follows: the polymer was prepared into a film, the film was thermally treated at 60° C., and the shape of the film was fixed for 3 minutes. Thereafter, the polymer was precipitated in water at a temperature between 35 to 40° C. in consideration of the melting point of the polymer to measure a length of the polymer in a restored state (top of FIG. 9B).

In another aspect, it can be seen that the shape-memory polymer material synthesized in Example 1 was deformed from the initial state when the shape-memory polymer material was thermally treated at a temperature of −20° C. which is less than or equal to the crystallization temperature (bottom of FIG. 9B)). Also, it can be seen that the shape-memory polymer material was restored to the initial state when the temperature was adjusted to an initial temperature of 35 to 40° C.

Next, the deformation recovery rate was measured.

The deformation recovery rate was defined by Equation 1 below, and is able to be used as an indicator for shape memory behavior of a polymer resin.

Deformation Recovery Rate $(Rr)=(Ie-Ir)/(Ie-Io)\times 100$     [Equation 1]

wherein:
Io: an initial length of a sample;
Ie: a length of a deformed sample; and
Ir: a length of the sample after recovery.

Therefore, as the deformation recovery rate of the 90% PCL-co-10% PGMA shape-memory polymer material treated with UV rays in Example 1-3 was greater than or equal to 90%, it can be seen that resilience is excellence, and that the shape-memory polymer material is suitable as a biomaterial due to its low melting point.

The invention claimed is:

1. A shape-memory polymer having a structure represented by the following Formula 1:

[Formula 1]

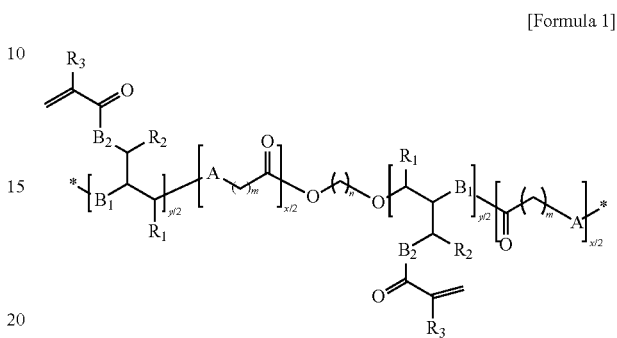

wherein $R_1$, $R_2$, and $R_3$ are each independently hydrogen (H) or an alkyl group having 1 to 6 carbon atoms;
m and n are each independently an integer ranging from 1 to 20;
A, $B_1$, and $B_2$ are each independently oxygen (O) or sulfur (S); and
each of x and y represents a molar percentage (mol %) of a repeating unit;
* means that

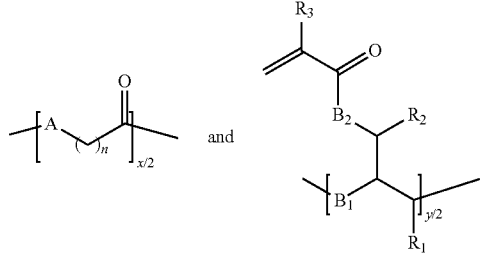

in formula 1 are repeated until x+y is 100;
provided that the sum of x and y is 100, and x is in a range of 80 to 98.

2. The shape-memory polymer of claim 1, wherein, in Formula 1, $R_1$, $R_2$, and $R_3$ are each independently hydrogen (H) or a methyl group;
m and n are each independently an integer ranging from 3 to 12;
A, $B_1$, and $B_2$ are each independently oxygen (O) or sulfur (S); and
each of x and y represents a molar percentage (mol %) of a repeating unit;
provided that the sum of x and y is 100, and x is in a range of 80 to 98.

3. The shape-memory polymer of claim 1, which has an average melting point of 30 to 49° C.

4. The shape-memory polymer of claim 1, which has an average melting point of 28 to 45° C. after a photo-cross-linking reaction.

5. The shape-memory polymer of claim 4, which has a deformation recovery rate of 90% or more at an average temperature of 28 to 45° C. after the photo-cross-linking reaction.

6. The shape-memory polymer of claim 1, wherein the structure represented by Formula 1 comprises a structure represented by the following Formula 2:

[Formula 2]

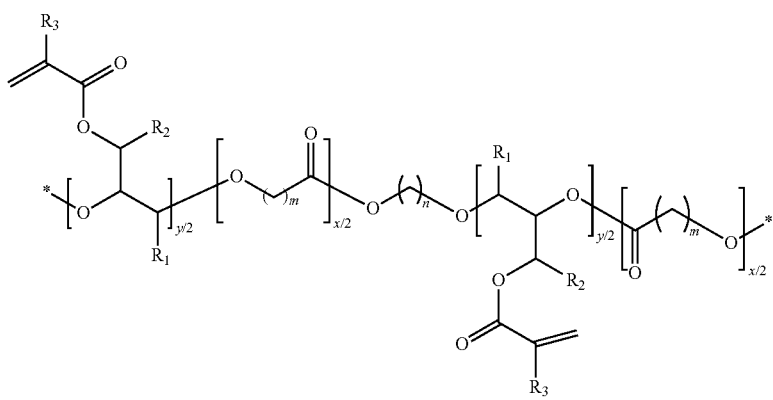

wherein $R_1$, $R_2$, and $R_a$ are each independently hydrogen (H) or an alkyl group having 1 to 6 carbon atoms;

m and n are each independently an integer ranging from 1 to 20;

each of x and y represents a molar percentage (mol %) of a repeating unit;

* means that

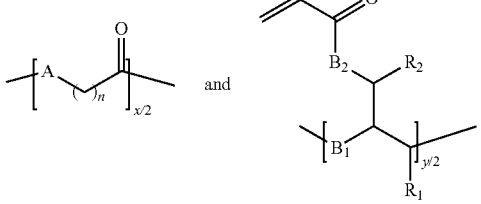

in Formula 2 are repeated until x+y is 100;

provided that the sum of x and y is 100, and x is in a range of 80 to 98.

7. A medical material comprising the shape-memory polymer defined in claim 1.

8. The medical material of claim 7, wherein the medical material is a support for blood vessel transplantation, a stent for blood vessel transplantation, a support for blood vessel anastomosis, a conduit for blood vessel transplantation, a material for tooth transplantation, a conduit for organ transplantation, a prosthesis for insertion into the human body, a prosthesis for spinal transplantation, a surgical suture, a carrier for drug delivery-or a nerve conduit.

9. A method for preparing a shape-memory polymer, the method comprising:

preparing a mixture comprising structures represented by Formulas 4 and 5 using the structure of Formula 6 as an initiator; and performing a ring-opening polymerization reaction of the structure of Formula 4 and the structure of Formula 5 in the presence of a catalyst to prepare a shape-memory polymer

[Formula 4]

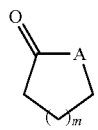

[Formula 5]

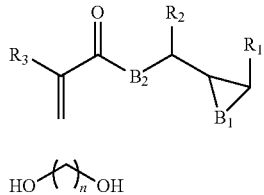

[Formula 6]

HO$\overbrace{\phantom{xx}}_n$OH wherein $R_1$, $R_2$, and $R_3$ are each independently hydrogen (H) or an alkyl group having 1 to 6 carbon atoms;

m and n are each independently an integer ranging from 1 to 20; and

A, $B_1$, and $B_2$ are each independently oxygen (O) or sulfur (S).

10. The method of claim 9, wherein the catalyst is 1,5,7-triazabicyclo[4.4.0]dec-5-ene (TBD), tin(II) (2-ethylhexanoate), trimethylopropane tris(3-mercaptopropionate), or zinc succinate.

11. The method of claim 9, further comprising:

inducing a photo-cross-linking reaction in the prepared shape-memory polymer.

12. The method of claim 9, wherein the ring-opening polymerization reaction is performed under the condition in which the reactant input ratio of the structure represented by Formula 4: the structure represented by Formula 5: the structure represented by Formula 6 is 78 to 90 moles: 10 to 22 moles: 0.5 mole.

* * * * *